United States Patent [19]
Krishnan et al.

[11] Patent Number: 5,627,329
[45] Date of Patent: May 6, 1997

[54] DETERMINATION OF DIFFUSION COEFFICIENT

[75] Inventors: Chandrasekhar Krishnan, Grand Island; Jian S. Qi, Amherst; Joseph A. Incavo, Snyder; William L. Reuter, Niagara Falls; Vivek Jain, Grand Island, all of N.Y.

[73] Assignee: Occidental Chemical Corporation, Niagara Falls, N.Y.

[21] Appl. No.: 527,609

[22] Filed: Sep. 13, 1995

[51] Int. Cl.$^6$ .................... G01N 15/00; G01N 13/00
[52] U.S. Cl. .................... 73/866; 73/19.02; 73/31.07
[58] Field of Search .................... 73/866, 38, 19.01, 73/19.02, 31.07, 23.41, 23.42

[56] References Cited

U.S. PATENT DOCUMENTS

| | | | |
|---|---|---|---|
| 3,926,561 | 12/1975 | Lucero | 73/38 |
| 4,944,180 | 7/1990 | Tou et al. | 73/38 |
| 5,157,960 | 10/1992 | Brehm et al. | 73/38 |
| 5,361,625 | 11/1994 | Ylvisaker | 73/38 |

OTHER PUBLICATIONS

*Abstract:* Article by D. Bobok et al. in Chem. Pap. 46(6), 363–7, 1992.

*Article:* "The Use of A Gas Chromatographic Technique For The Study of Diffusion In Polymers," by PJT Tait et al., *Journal of Chromatographic Science*, vol. 17, pp. 219–223 (Apr. 1979).

*Article:* "Size Effects On Solvent Diffusion In Polymers," by D Arnould et al., *Ind. Eng. Res.*, 31, pp. 218–228, (1992).

*Article:* "Diffusion of Organic Vapors At Low Concentrations In Glassy PVC, Polystyrene, and PMMA," by AR Berens et al., *Journal of Membrane Science*, 10, pp. 283–303 (1982).

*Article:* "Diffusion and Relaxation In Glassy Polymer Powders: 1. Fickian Diffusion of Vinyl Chloride In Poly(Vinyl Chloride)." AR Berens, *Polymer*, vol. 18, pp. 697–704, (Jul. 1977).

*Primary Examiner*—Hezron E. Williams
*Assistant Examiner*—Nashmiya Ashraf
*Attorney, Agent, or Firm*—Richard D. Fuerle

[57] ABSTRACT

Disclosed is a method of determining a diffusion coefficient for a diffusant in a particulate. An inert gas is passed through a particulate containing the diffusant. A parameter that is proportional to the concentration of the diffusant in the inert gas is measured over a period of time and the slope of the linear portion of that relationship is determined and is multiplied by a constant.

20 Claims, 2 Drawing Sheets

DETERMINATION OF DIFFUSION COEFFICIENT

BACKGROUND OF THE INVENTION

This invention relates to a method of determining the diffusion coefficient of a diffusant in a solid particulate. In particular, it relates to passing an inert gas through a bed of particulates containing a diffusant, measuring over time a parameter proportional to the diffusant concentration in the effluent gas, determining the slope of the linear portion of that relationship, and multiplying that slope by a constant.

A diffusion coefficient indicates the rate at which a diffusant moves through a medium under a concentration gradient at a particular temperature and pressure. The diffusion of a chemical through a solid particulate is encountered in numerous industrial processes. Diffusion coefficients often must be known to properly design and operate these processes. For example, in a polyethylene manufacturing process, polymerization occurs in a flammable hydrocarbon solvent such as hexane. After the polymerization, the hexane solvent must be separated and recovered from the polymer to provide a clean resin product. The resin, usually in a form of powder, must be dried to a very low level to minimize the emission of hexane to the environment and the risk of explosion due to hexane build-up in storage vessels. When the hexane in the polyethylene is below 5%, the drying process becomes essentially a process of hexane diffusion in the polymer. The diffusion coefficient therefore is needed to properly design and optimize the process. As another example, crude poly(vinyl chloride) resins usually contain vinyl chloride monomer, a carcinogen. Its diffusion coefficient is needed to determine the conditions required to reduce the toxic vinyl chloride monomer concentration to a safe level.

Most conventional methods of measuring the diffusion coefficient in a plastic material are based on a film permeability method similar to ASTM D 1434. In such a method, a film made of the plastic material is placed between two chambers, one of which holds a constant concentration of the diffusant gas. The diffusant permeates through the film into the other chamber and, by measuring the diffusant concentration in the second chamber, one can obtain the diffusion coefficient. Although this method can produce good precision and accuracy for many practical applications, it has serious shortcomings if casting a film changes the morphology and physicochemical characteristics (such as crystallinity) of the material and if data for unaltered particulates are desired. In addition, at high temperatures and pressures, the mechanical integrity of the film may become a problem. And, for some materials, making a mechanically sustainable film simply is not possible.

Diffusion coefficients for large solids can be determined by measuring the gain or loss in weight of the solid over time as the diffusant enters or leaves the solid. The accuracy of this method becomes questionable when the diffusant concentration is low. Although the method can also be used to measure the diffusion coefficients for fine particulates, its accuracy falls due to interparticle contacts and interactions, and poor ventilation at those points.

Diffusion coefficients of polymer particulates can also be determined by, for example, packing a column with polymer-coated inert beads free of the diffusant, and chromatographing the diffusant by means of partitioning it between the polymer-coated beads and an inert carrier gas. The accuracy of that method also suffers because it requires coating inert particles, which changes the morphology of the polymer and may significantly affect diffusivity.

SUMMARY OF THE INVENTION

We have discovered a method of measuring the diffusion coefficient for particles without altering them. The method is simple yet much more accurate than prior methods, especially for small particles. Our method allows accurate measurements of intrinsic diffusion coefficients for particulates without forming the particulates into films.

Moreover, in the method of this invention, it is not necessary to know the actual diffusant concentration in the solid, nor in the gas phase, making the method easier and simpler to carry out. That is a major advantage because it is generally very difficult and time-consuming to precisely measure the actual concentration of a fast diffusant in fine particles, particularly at elevated temperatures. For a fast diffusant, careful handling of the solids is required to avoid any loss of the diffusant prior to measurements. However, in the method of this invention, one needs to measure only a parameter that is proportional to the diffusant concentration in an inert gas that passes over the particles, something that is much more easily accomplished.

The method of this invention can also be used to duplicate actual industrial gas/solid flow conditions, and determine the apparent diffusion coefficients under those conditions. These apparent or effective diffusion coefficients can then be used to determine the actual process efficiently under the industrial conditions.

DESCRIPTION OF THE PREFERRED EMBODIMENTS

Figure 1:
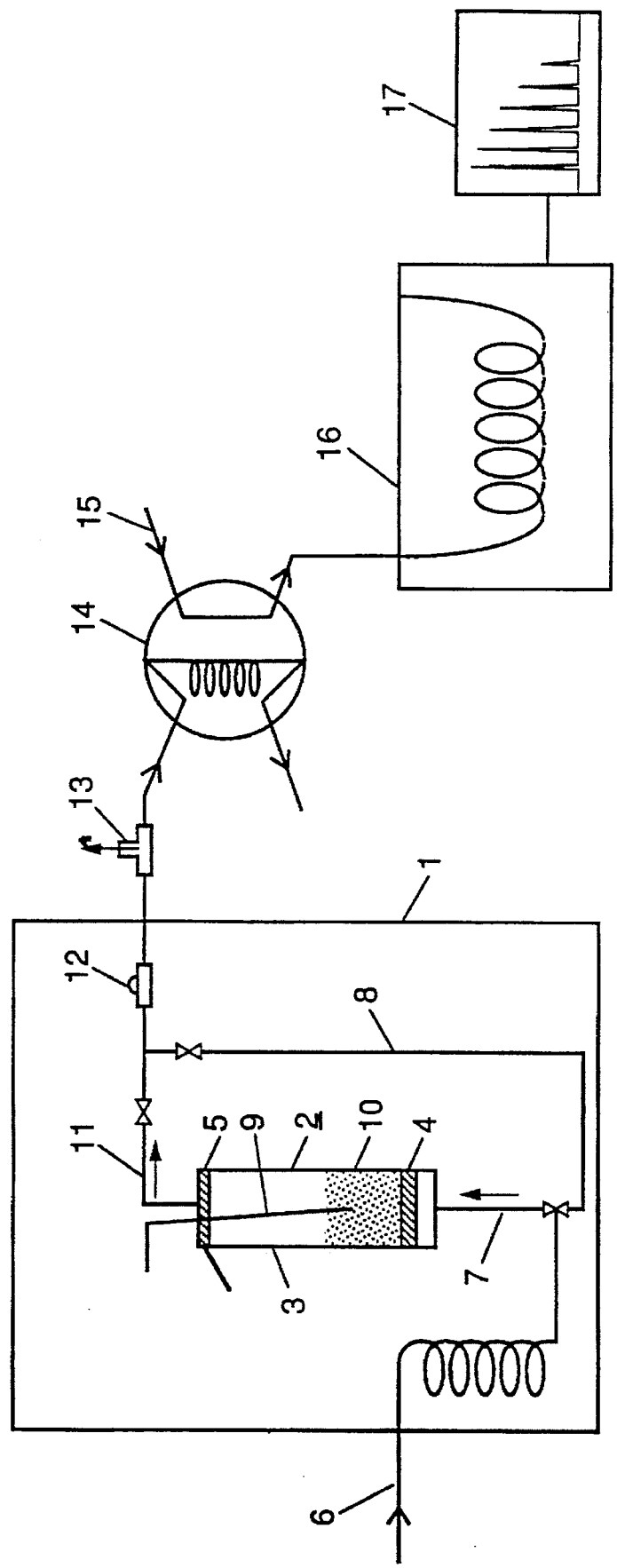
FIG. 1 is a diagrammatic side view illustrating the apparatus used to perform experiments described in the examples.

In FIG. 1, a temperature controlled oven 1 contains a fluidized bed 2 which consists of a glass cylinder 3 and a gas pervious glass frit diffuser plate 4, with a seal 5 at the top. Nitrogen from line 6 enters the oven and is split into line 7, which goes to fluidized bed 2, and bypass 8. A thermometer 9 measures the temperature of the powder 10 in fluidized bed 2. The nitrogen passes out of fluidized bed 2 through line 11, pass filter 12, and can be vented at valve 13. It can enter 6-port sampling valve 14 where helium in line 15 takes the diffusant into gas chromatograph (GC) 16. The results from the gas chromatograph are shown at 17, a plot of time versus a parameter proportional to the concentration of the diffusant in the nitrogen, in this case the GC area counts.

The method of this invention can be used to determine the diffusion coefficient of a diffusant in a particulate. A practical range of sizes for the particulate is about 10 to about 5000 microns. While larger or smaller sized particles can be used, that range of particle sizes is considered to be practical because if the particle size is too small the time during which the measurements must be taken may be too short for on-line measurements. If the particle size is too large, precision is not impaired, but a very long time may be required to conduct the measurements. The invention is particularly useful with particulates having a diameter of about 10 to about 500 microns as it is difficult to determine the diffusion coefficient by other methods for particles within that size range. To obtain the most accurate results, the distribution of particle sizes in the samples tested should be as narrow as possible. A very narrow particle size distribution can be obtained, for example, by sieving a larger sample, taking a fraction, and re-sieving that fraction. Preferably, the particle size distribution of the particulate should be within 10% of the mean particle size.

While the method of this invention can be applied to particles of almost any shape, it is most usefully applied to spherical particles or particles that are approximately spherical, such as cylinders (where height≈diameter) or cubes. The particles may be of any solid material that is capable of absorbing a diffusant, such as wood, plastics, metals, and inorganic materials. Polymeric particulates, such as polyethylene, poly(vinylchloride), polyurethane, polystyrene, polyesters, and polymethylmethacrylate, are preferred as the invention is most applicable to that type of material.

The diffusant can be a gas or a liquid, but it must leave the particle in a gaseous state. Thus, if the diffusant is not very volatile, it may be necessary to heat the particles. The initial concentration distribution of the diffusant throughout the particle must be uniform for accurate measurements. This can be accomplished by letting the particles sit in a closed atmosphere containing a constant diffusant concentration until equilibrium has been reached. Preferably, the particles are not saturated with diffusant because excessive adsorption of diffusant may swell the particles or otherwise alter their geometry and other physicochemical characteristics. A diffusant concentration of about 5 to about 40 wt % of saturation is preferred. Organic compounds, such as the $C_2$ to $C_{10}$ alkanes and alkenes, are commonly encountered diffusants.

Any inert gas that does not react with or interact with the diffusant or the particles can be used in the process of this invention. Examples of such gases may include nitrogen, argon, helium, carbon dioxide, and air.

The diffusion coefficient depends upon the temperature of the particles. The particles and the diffusion cell can be heated in an oven and the inert gas should preferably be heated to the same temperature as the particles. Generally, any temperature at which the diffusant does not condense into a liquid and which does not melt or soften the particles can be used. However, lower temperature is desirable if the particles are very small or the diffusant diffuses rapidly since a low temperature allows more time for the measurements. On the other hand, if the particles are large or the diffusion rate is low, a higher temperature can be used to shorten the experimental time. Most often, the temperature chosen is the temperature for the process to be studied.

The analytical device which measures a parameter proportional to the concentration of the diffusant in the inert gas (where the parameter can be the concentration itself) can be of any type including, for example, gas chromatography (GC), photometric measurement (where the parameter is intensity of light absorbed or scattered), or chemical detector (where the parameter is the concentration of diffusant detected). Since at least two measurements must be taken and the interval between the measurements must be short if the particles are small, it is preferable to use a gas chromatograph as the analytical device. A gas chromatograph can be set up to automatically measure the parameter (GC area counts) three times per minute or more, thereby permitting a precise measurement of the diffusion coefficient of very small particles. A gas chromatograph is preferred because the capillary column contained in it focuses the gaseous diffusant injected into a discrete peak, which can be readily quantified as the area under the peak.

The two or more measurements give the parameter proportional to the concentration of the diffusant in the inert gas for an interval of time. After a small initial time, the change in the natural log of the parameter per unit time (i.e., the slope of the plot of the natural log of GC area points versus time) will become constant. It is this constant or linear portion of the slope that is used to calculate the diffusion coefficient. The calculation is very simply made by multiplying the slope by a constant. For a spherical or near-spherical particle that constant is $-R^2/\pi^2$ where R is the average radius of a particle. If the particles are in the form of flakes the constant is $-4l^2/\pi^2$, where 1 is flake thickness, and if the particles are in the form of needles the constant is $-R^2/2.4$, where R is the average radius of the needles. Other geometries can be approximated by an equivalent radius using the constant for a spherical particle.

The particles, having the diffusant uniformly dispersed throughout, are placed in a fluidized bed. A sufficient amount of particles should be used so that the measured parameter is easily detectable. After reaching equilibrium at the desired temperature, the inert gas is passed through the particles. If the inherent diffusion coefficient is to be determined, the inert gas should fluidize the particles so that the entire surface of each particle is in thorough contact with the flowing gas. We have found that inherent diffusion coefficients obtained by the method of this invention correspond closely to inherent diffusion coefficients obtained for the same solids and diffusants by other methods. However, since in actual industrial operations the particles may be treated under conditions in which they are not completely fluidized, those conditions can be duplicated in the method of this invention by using the inert gas at a lower velocity so that the particles are either stationary or only partly fluidized. In this way, an apparent or effective diffusion coefficient is obtained which will enable one to make accurate calculations of the corresponding industrial set up.

The following examples further illustrate this invention.

EXAMPLE 1

As shown in FIG. 1, a sample cell 9 cm×2.7 cm×2.5 cm having porous glass frit at the bottom and a glass fiber filter at its outlet was filled with either a 0.25 gm or a 1 gm sample of polyethylene powder containing hexane and placed in a temperature controlled oven. (In some experiments a copper tube with a steel mesh screen at the bottom was used instead of the glass cell.) Nitrogen gas was preheated to the desired temperature using a temperature controlled oil bath prior to entering the oven. Hexane concentration in the exiting nitrogen stream was monitored by a gas chromatograph equipped with a flame ionization detector. The GC was modified by installing a valve compartment which automated the control of a 6-port Valco valve equipped with a 500 µl sample loop for sampling purposes. The sample loop was continuously flushed by the process stream with the aid of a Gorman-Rupp chemical feed bellows pump. A 15 m dimethyl silicone fused silica capillary column was used for analysis. The injection port was operated in a splitless mode. Helium was used as a carrier gas at 4 ml/min. The column temperature was 60° C. isothermal. Injection port and detector temperatures were 225° C. and 250° C., respectively. The sample valve was programmed for three automatic injections per minute. The concentration decay trace was recorded on an integrator which measured the area of the hexane response peak. The sensitivity of the GC system was about 250 ppb hexane in nitrogen. The sample line was purged with dry nitrogen prior to an experimental run and was injected as a blank to assure cleanliness. Calibration standards were prepared by diluting a 4990 ppm (mole %) hexane standard in nitrogen obtained from Scott Gases.

To insure that the powder sample had a narrow particle size distribution, it was sieved into various fractions. One of the fractions was chosen and re-sieved. The desired fraction from the second sieving was then analyzed by an optical technique. Usually, two sievings were sufficient to obtain the particle size distribution within 10% deviation of the mean.

A known amount of reagent grade n-hexane (99+%) was spiked into a hexane-free polyethylene powder sample. The hexane concentration of the powder was in the range of 3500 to 5000 ppm as determined by headspace analysis or calculation. The oven was set to the desired temperature, which typically took 10 to 15 minutes. Once that temperature had been obtained, the cell was held for an additional two to five hours at that temperature. The nitrogen flow was set using a rotameter and made to flow through the bypass to check that its temperature was the same as the cell temperature. The nitrogen was then made to flow through the cell and the gas chromatogram was begun. It was experimentally determined that the optimum nitrogen flow was about 2000 cc/min for complete fluidization of the bed. The following table gives the results at the various temperatures, nitrogen flow rates, and particle sizes.

| $N_2$ Flow (cc/min) | Observed D ($cm^2$/s) |
|---|---|
| RESULTS AT 60° C. | |
| 500 | 0.65E-8, 0.64E-8, 0.65E-8 (mean = 0.65E-8) |
| 1000 | 1.9E-8, 1.93E-8, 1.83E-8 (mean = 1.89E-8) |
| 1500 | 2.8E-8, 3.1E-8, 2.8E-8 (mean = 2.9E-8) |
| 2000 | 3.1E-8, 3.0E-8, 3.3E-8 (mean = 3.13E-8) |
| 2500 | 3.2E-8, 3.0E-8, 3.1E-8 (mean = 3.1E-8) |
| 3000 | 3.2E-8, 3.0E-8, 3.2E-8 (mean = 3.1E-8) |
| 2000** | 3.1E-8 |
| RESULTS AT 70° C. | |
| 500 | 0.74E-8, 0.73E-8 |
| 1000 | 2.2E-8 |
| 1500 | 3.7E-8 |
| 2000 | 6.0E-8 |
| 2500 | 5.9E-8, 5.5E-8, 5.9E-8 (mean = 5.8E-8) |
| 3000 | 5.8E-8, 5.9E-8, 5.7E-8 (mean = 5.8E-8) |
| 2000** | 5.5E-8 |

| $N_2$ Flow (cc/min) | PE Amount (g) | Observed D ($cm^2$/s) |
|---|---|---|
| RESULTS AT 80° C. | | |
| 300 | 1.0 | 1.3E-8 |
| 2000 | 1.0 | 4.7E-8 |
| 3500 | 0.25 | 1.1E-7 |
| RESULTS AT 93° C. | | |
| 300 | 1.0 | 1.9E-8 |
| 1300 | 1.0 | 3.6E-8 |
| 2000 | 1.0 | 6.7E-8 |

**All runs used 127 μm powder except that this run used 74 μm powder.

In the table "Observed D" means the diffusion coefficient as calculated by observing the GC area points, determining the slope of the natural log of the area points versus time, and multiplying that slope by $-R^2/\pi^2$, where R is particle diameter in centimeters.

The above tables show observed D values for n-hexane in polyethylene in the 60°–93° C. temperature range as a function of the flow rates.

Figure 2:
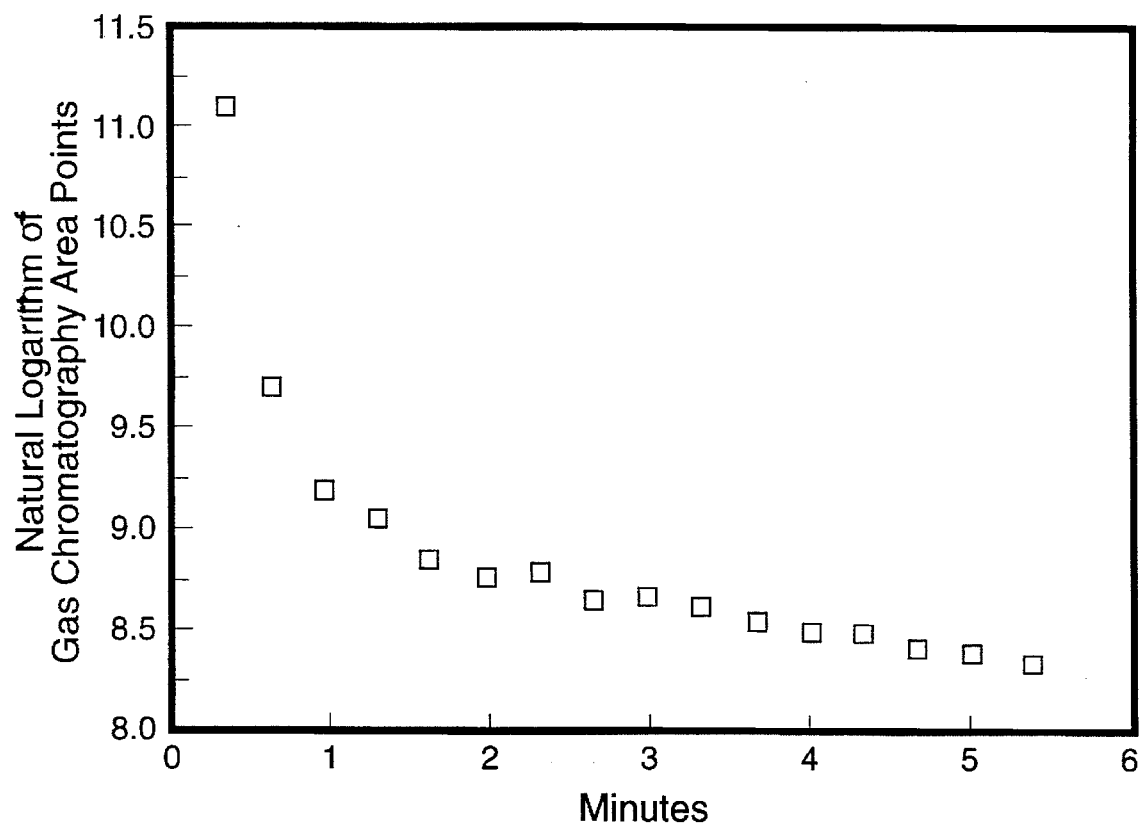
FIG. 2 is a graph of the experimental concentration decay profile of n-hexane in 127 μm polyethylene powder at 70° C. The graph is a plot of the natural log of the GC area counts against time.

Referring to FIG. 2, the ordinate is the natural logarithm of gas chromatography (GC) area points, a parameter proportional to the concentration of the n-hexane in the nitrogen gas, and the abscissa is time in minutes. The slope of the linear portion of the Curve in FIG. 2 was determined to be $-0.0142$ seconds$^{-1}$. Since the particle size was 127 μm, R was 63.5 μm (or 0.00635 cm), $-R^2/\pi^2$ was $-4.0855 \times 10^{-6}$ $cm^2$), and D (the intrinsic diffusion coefficient) was the slope times $-R^2/\pi^2$ or $5.8 \times 10^{-8}$ $cm^2$/sec.

The intrinsic diffusion coefficient for n-hexane/polyethylene was independently determined by M. Markelov and B. Kogarko of ACS Labs by the film permeation or time-lag method in "Service Report to OxyChem: Diffusion, Permeability and Solubility of n-hexane in Polyethylene", May 1995. The value determined was $5.7 \times 10^{-8}$ $cm^2$/sec. at 70° C.

We claim:

1. A method of determining a diffusion coefficient for a diffusant in a particulate comprising
    (A) passing an inert gas through said particulate containing said diffusant;
    (B) measuring over time a parameter that is proportional to the concentration of said diffusant in said inert gas to produce a relationship between time and said parameter, said relationship having a linear portion and a non-linear portion;
    (C) determining the slope of said linear portion of said relationship; and
    (D) multiplying said slope by a constant, whereby the product is said diffusion coefficient.

2. A method according to claim 1 wherein said inert gas fluidizes said particulate and said diffusion coefficient is the intrinsic diffusion coefficient.

3. A method according to claim 1 wherein said inert gas does not completely fluidize said particulate and said diffusion coefficient is a apparent diffusion coefficient.

4. A method according to claim 1 wherein said particulate is treated as spherical and said constant is $-R^2/\pi^2$ where R is the average radius of particles of said particulate.

5. A method according to claim 1 wherein the particle size distribution of said particulate is within 10% of the mean particle size of said particulate.

6. A method according to claim 1 wherein said measuring is performed by a gas chromatograph and said parameter is gas chromatography area counts.

7. A method according to claim 1 wherein said inert gas is nitrogen.

8. A method according to claim 1 wherein said particulate is a polymer.

9. A method according to claim 8 wherein said particulate is polyethylene and said diffusant is a solvent.

10. A method according to claim 9 wherein said solvent is hexane.

11. A method according to claim 8 wherein said particulate is polyvinyl chloride and said diffusant is vinyl chloride monomer.

12. A method according to claim 1 wherein said particulate has a particle size of about 10 microns to about 3000 microns.

13. A method according to claim 1 wherein the concentration of said diffusant in said particulate is about 5 to about 40 wt % of saturation.

14. A method according to claim 1 wherein said inert gas flows through said particulate at about 2000 cc/min.

15. A method of determining a diffusion coefficient of a diffusant in approximately spherical solid particles of approximately uniform diameter comprising
    (A) placing said particles containing a uniformly dispersed concentration of said diffusant on a gas pervious horizontal diffusor plate;

(B) passing an inert gas up through said diffusor plate and through said particles;

(C) measuring at at least two non-initial times a parameter proportional to the concentration of said diffusant in said inert gas;

(D) determining the change in that parameter per unit time; and (E) multiplying said change per unit time by $-R^2/\pi^2$, where R is the average radius of said particles and the product is said diffusion coefficient.

16. A method according to claim 15 wherein said inert gas fluidizes said particles.

17. A method according to claim 15 wherein said particles have a diameter of about 10 to about 500 microns.

18. A method according to claim 15 wherein said measuring is performed by a gas chromatograph and said parameter is gas chromatography area points.

19. A method according to claim 15 wherein the concentration of said diffusant in said particles is about 5 to about 40 wt % of saturation.

20. A method of determining the intrinsic diffusion coefficient of a diffusant in a solid spherical particulate material having an average particle size between about 10 microns and about 500 microns comprising (A) diffusing said diffusant into said particulate material to produce a uniform concentration of about 5 to about 40 wt % of saturation;

(B) placing said particulate material in a fluidized bed;

(C) fluidizing said particulate material with an inert gas;

(D) using a gas chromatograph, measuring the rate of change of the gas chromatography area points of said diffusant in said inert gas; and (E) when said rate is constant over time, multiplying said rate by $-R^2/\pi^2$, where R is the average radius of said particulate material and the product is said intrinsic diffusion coefficient.

* * * * *